US006795456B2

(12) United States Patent
Scaggs

(10) Patent No.: US 6,795,456 B2
(45) Date of Patent: Sep. 21, 2004

(54) 157 NM LASER SYSTEM AND METHOD FOR MULTI-LAYER SEMICONDUCTOR FAILURE ANALYSIS

(75) Inventor: Michael J. Scaggs, Weston, FL (US)

(73) Assignee: Lambda Physik AG, Goettingen (DE)

( * ) Notice: Subject to any disclaimer, the term of this patent is extended or adjusted under 35 U.S.C. 154(b) by 128 days.

(21) Appl. No.: 09/733,874

(22) Filed: Dec. 8, 2000

(65) Prior Publication Data

US 2001/0030981 A1 Oct. 18, 2001

Related U.S. Application Data

(60) Provisional application No. 60/172,674, filed on Dec. 20, 1999.

(51) Int. Cl.[7] ................................................. H05B 7/00
(52) U.S. Cl. ...................... 372/23; 372/57; 250/492.22
(58) Field of Search ............................. 372/23, 55, 57, 372/61; 250/491.1, 492.22, 492.23; 204/298.32

(56) References Cited

U.S. PATENT DOCUMENTS

| | | | | |
|---|---|---|---|---|
| 4,258,334 A | | 3/1981 | McCusker et al. | 331/94.5 C |
| 4,393,505 A | | 7/1983 | Fahlen | 372/57 |
| 4,616,908 A | | 10/1986 | King | 350/576 |
| 5,051,558 A | | 9/1991 | Sukhman | 219/121.68 |
| 5,057,184 A | | 10/1991 | Gupta et al. | 156/637 |
| 5,221,823 A | | 6/1993 | Usui | 219/121.78 |
| 5,440,587 A | | 8/1995 | Ishikawa et al. | 375/332 |
| 5,450,436 A | | 9/1995 | Mizoguchi et al. | 372/59 |
| 5,559,584 A | | 9/1996 | Miyaji et al. | 355/73 |
| 5,590,146 A | | 12/1996 | von Borstel | 372/58 |
| 5,593,606 A | | 1/1997 | Owen et al. | 219/121.71 |
| 5,761,236 A | | 6/1998 | Kleinschmidt et al. | 372/100 |
| 5,763,855 A | | 6/1998 | Shioji | 219/121.84 |
| 5,766,497 A | * | 6/1998 | Mitwalsky et al. | 216/56 |
| 5,811,753 A | | 9/1998 | Weick et al. | 219/121.78 |
| 5,841,099 A | | 11/1998 | Owen et al. | 219/121.69 |
| 2002/0176469 A1 | * | 11/2002 | Vogler et al. | 372/61 |

FOREIGN PATENT DOCUMENTS

| | | | |
|---|---|---|---|
| EP | 0 790 681 A2 | 8/1997 | H01S/3/134 |
| EP | 1 017 086 A1 | 7/2000 | H01L/21/057 |
| JP | 408055792 A | 2/1996 | H01L/21/027 |
| WO | WO 98/57213 | 12/1998 | G02B/27/00 |
| WO | WO 98/59364 | 12/1998 | H01L/21/027 |
| WO | WO 99/04467 | 1/1999 | H01S/3/134 |
| WO | WO 99/08133 | 2/1999 | G03B/27/42 |

OTHER PUBLICATIONS

Kakehata et al., "Efficiency Characterization of Vacuum Ultraviolet Molecular Fluorine (F2) Laser (157 nm) Excited by an Intense Electric Discharge", IEEE Journal of Quantum Electronics, vol. 27, Issue 11, Nov. 1991, p. (s): 2456–2464.*

T. Y. Chang, "Improved Uniform–Field Electrode Profiles for TEA Laser and High–Voltage Applications," *The Review of Scientific Instruments*, vol. 44, No. 4, Apr. 1973, pp. 405–407.

*Applied Physics Letters*, vol. 31, No. 1, Jul. 1, 1977, "vuv emissions from mixtures of $F_2$ and the noble gasses—A molecular $F_2$ laser at 1575 Å," James K. Rice, A. Kay Hays, and Joseph R. Woodwsorth, 5 pgs.

(List continued on next page.)

*Primary Examiner*—Jerome Jackson
*Assistant Examiner*—José R. Diaz
(74) *Attorney, Agent, or Firm*—Stallman & Pollock LLP

(57) ABSTRACT

A failure analysis system and method for multi-layer semiconductor devices, including a molecular fluorine laser system for producing a 157 nm beam and an imaging system for imaging the beam onto the semiconductor device. The laser beam etches away one or more top (passivation) layers to expose layers disposed underneath. Circuitry formed in exposed layers can then be tested.

3 Claims, 2 Drawing Sheets

OTHER PUBLICATIONS

*The Journal of Chemical Physics*, vol. 69, Sep. 15, 1978, "An efficient, high power $F_2$ laser near 157 nm[a]," Joseph R. Woodworth and James K. Rice, pp. 2500–2504.

*Optics Communications*, vol. 28, No. 1, Jan. 1979, "Discharge pumped $F_2$ Laser at 1580 Å", H. Pummer, K. Hohla, M. Diegelmann and J.P. Reilly, pp. 104–106.

*Journal of Applied Physics*, vol. 50, Jun. 1979, No. 6, "Novel neutral atomic fluorine laser lines in a high–pressure mixture of $F_2$ and He," Shin Sumida, Minoru Obara, and Tomoo Fujioka, pp. 3884–3887.

*Optics and Laser Technology*, vol. 11, No. 6, Dec. 1979, "CIF and $F_2$: two new ultra–violet laser systems," K. Hohla, M. Diegelmann, H. Pummer, K.L. Kompa, pp. 305–310.

*Applied Optics VUV VI*, vol. 19, No. 23, Dec. 1, 1980, "Vacuum ultraviolet excimer lasers," M.H.R. Hutchinson, pp. 3883–3888.

James K. Rice, et al., "Oscillator Performance and Energy Extraction from a KrF Laser Pumped by a High–Intensity Relativistic Electron Beam," *IEEEE Journal of Quantum Electronics*, vol. QE–16 No. 12, Dec. 1980.

E. A. Stappaerts, "Novel Analytical Design for Discharge Laser Electrode Profiles," *Appl. Phys. Lett.*, vol. 40, No. 12, Jun. 15, 1982, pp. 1018–1019.

*Journal of Applied Physics*, vol. 53, May 1982, No. 5, "Gain and saturation of the atomic fluorine laser," R. Sadighi–Bonabi, F.W. Lee, and C.B. Collins, pp. 3418–3423.

G. J. Ernst, "Compact Uniform Field Electrode Profiles," *Optics Communications*, vol. 47, No. 1, Aug. 1, 1983, pp. 47–51.

G. J. Ernst, "Uniform–Field Electrodes with Minimum Width," *Optics Communications*, vol. 49, No. 4, Mar. 15, 1984, pp. 275–277.

*Applied Physics*, Vo. B33, No. 4, Apr. 1984, "Intense Laser Generation From an Atomic–Fluorine," I.G. Koprinkov, K.V. Stamenov, and K.A. Stankov, pp. 235–238.

*Review of Scientific Instruments*, vol. 56, No. 5, May 1985, "Simple, compact, high–repetition rat XeCI laser," E. Armandillo, G. Grasso, and G. Salvetti, pp. 674–676.

*Optics Communications*, vol. 55, No. 6, Oct. 15, 1985, "Gain Measurements at 157 nm in an $F_2$ Pulsed Discharge Molecular Laser," A.C. Cefalas, C. Skordoulis, M. Kompitasas and C.A. Nicolaides, pp. 423–426.

McKee, T., "Spectral–narrowing Techniques for Excimer Laser Oscillators," *CAN. J. Phys.*, vol. 63, 1985, pp. 214–219.

*Soviet Journal for Quantum Electronics*, 16(5) May 1986, "High–power efficient vacuum ultraviolet $F_2$ laser excited by an electric discharge," V.N. Ishchenko, S.A. Kochubei, and A.M. Razhev, pp. 707–709.

Ishchenko, V. N., et al., "High–power Efficient Vacuum Ultraviolet F2 Laser Excited by an Electric Discharge," *Sov. J. Quantum Electron*, 167(5), May 1986, pp. 707–709.

ZOS, Akademie der Wissenschaften der DDR, Zentralinstitut fur Optik und Wissenschaften der DDR, Oktober 1987, "Leistungastarker atomarer Fluorlaser im roten Spektralbereich," Jurgen Lademann, Roland Kunig, Wadim Saidow, Rainer Weidauer, 12 pgs.

S. Küper, "Ablation of Polytetrafluoroethylene (Teflon) with Femtosecond UV Excimer Laser Pulses," *Appl. Phys. Lett.*, vol. 54, No. 1, Jan. 2, 1989, pp. 4–6.

*Discharge–Pumped Excimer Laser Research in Japan*, Apr. 1988, "Theoretical simulation of a discharge pumped $F_2$ excimer laser," T. Uematsu et al. Keio U., 5 pages.

*Conference on Lasers and Electro–Optics*, 1989 Technical Digest Series, vol. 11, "Intense VUV–XUV generation from rare gas excimers," Wataru Sasaki, Kou Kurosawa, 23 pgs.

*Applied Physics Letters*, vol. 54, Feb. 13, 1989, No. 7, "High–power discharge–pumped $F_2$ molecular laser," Kawakatsu Yamada, Kenzo Miyazaki, Toshifumi Hasama, and Takuzo Sata, 6 pgs.

*Leos '89, Lasers and Electro–Optics Society Annual Meeting Conference Proceedings*, Oct. 17–20, 1989, "High Power Discharge–Pumped $F_2$ Laser," K. Yamada, K. Miyazaki, T. Hasam, T. Sato, M. Kasamatsu, and Y. Mitsuhashi, 13 pgs.

*Science Report, LAMBDAPHYSIK*, No. 3, Nov. 1990, "Breakthrough in $F_2$Laser Technology," 2 pgs.

*Verhandlungen*, Mar. 1990, Phsyikertagung Munchen.

*Applied Physics Letters*, vol. 56, Jun. 25, 1990, No. 26, "High specific output energy operation of a vacuum ultraviolet molecular fluorine laser excited at 66 MW/cm$^3$ by an electric discharge," Masayuki Kakehata, Etsu Hashimoto, Fumihiko Kannari and Minoru Obara, 6 pgs.

*Journal of Modern Optics*, vol. 37, No. 4, Apr. 1990, "Amplification characteristics of a discharge excited $F_2$ laser," C. Skordoulis, E. Sarantopoulou, S. Spyrou and A.C. Cefalas, pp. 501–509.

*Gas Flow and Chemical Lasers*, SPIE Vo. 1397, Sep. 10–14, 1990, "Frequency up–conversion of a discharge pumped molecular fluorine laser by stimulated Raman scattering in $H_2$," Masayuki Kakehata, Etsu Hashimoto, Fumihiko Kannari, and Minoru Obara, pp. 185–189.

*Conference on Lasers and Electro–optics*, 1990 Technical Digest Series, vol. 7, May 21–25, 1990, "Spectroscopic comparison between low and high pressure discharge pumped Xe atomic lasers," K. Komatsu, E. Matsui, S. Takahashi, Fumiko Kannari, M. Obara, 30 pgs.

Institut Fur Quantenoptik, Oct. 22, 1991, "Stimulated Raman scattering of a $F_2$–Laser in $H_2$," C. Momma, A. Tunnermann, F. Vo__, C. Windolph and B. Wellegehausen, 8 pgs.

*Tagunsband*, Vom, 24, Bis. 26, Sep. 1991, Abstract: "Vakuum UV Molekullaser mit hoher Ausgangsleistung," 3 pgs.

*HIGHLIGHTS, LAMBDAPHYSIK*, No. 29, Jun. 1991, "VUV Spectroscopy by Frequency Tripling," 6 pgs.

*IEEE Journal of Quantum Electronics*, Nov. 1991, vol. 27, No. 11, "Efficiency Characterization of Vacuum Ultraviolet Molecular Fluorine ($F_2$) Laser (157 nm) Excited by an Intense Electric Discharge," Masayuki Kakehata, Tatsuya Uematsu, Fumihiko Kannari, and Minoru Ohara, pp. 2456–2464.

*HIGHLIGHTS, LAMBDAPHYSIK*, No. 33, Feb. 1992, "VUV Stokes and Anti–Stokes Raman Lines Derived from an $F_2$ Laser," C. Momman, A. Tunermann, F. Vo__, C. Windolph, and B. Wellegehausen, 5 pgs.

*The Journal of Physical Chemistry*, vol. 96, No. 15, Jul. 23, 1992, "Dissociation Rate Constants of Alkylbenzenes from Hot Molecules Formed by 158–nm ($F_2$ Laser) Irradiation," Tetsuya Shimada, Yuichi Ojima, Nobuaki Nakashima, Yasukazu Izawa, and Chiyoe Yamanaka, 10 pgs.

"Gas Flow and Chemical Lasers," vol. 1810, Sep. 21–25, 1992, "Theoretical Anti–Stokes Conversion of VUV Spectrum by Dual–Wavelength Pumped Stimulated Raman Scattering," Tsuneo Nakata, Fumihiko Kannari, and Minoru Obara, 18 pgs.

*Chemistry Letters*, No. 7, 1992, "Photolysis of $CO_2$ with 158 nm ($F_2$ Laser. Reactivity of O ($^1$D) with $CH_4$, $CF_3H$, and $CF_3CH_3$," Masanobu Kojima, Yuichi Ojima, Nobuaki Nakashima, Yasukazu Izawa, Toru Akano, and Chiyoi Yamanaka, 10 pgs.

S.M. Hooker et al., "Influence of Cavity Configuration on the Pulse Energy of a High–Pressure Molecular Fluorine Laser," *Appl. Phys..*, vol. B55, No. 1, Jul. 1992, pp. 54–59.

*The Journal of Chemical Physics*, vol. 98, No. 11, Jun. 1993, "Laser photolysis of benzene at 158 nm," Tetsuya Shimada, Nobuaki Nakashima, Yasukazu, Izawa, and Chiyoe Yamanaka, pp. 438–440.

*Applied Physics Letters*, vol. 63, No. 4, Jul. 26, 1993, "Small–signal gain measurements in an electron beam pumped $F_2$ laser," H.M.J. Bastiaens, B.NM.C. van Dam, P.J.M. Peters, and W. J. Witteman, 7 pgs.

*HIGHLIGHTS LAMBDAPHYSIK*, Apr. 1993, "Excimer laser based microstructuring using mask projection techniques," U. Sarbach and H.J. Kahlert, 4 pgs.

*HIGHLIGHTS, LAMBDAPHYSIK*, No. 43, Jan. 1994, "Photochemical modification of Fluorocarbon Resin to Generate Adhesive Properties," 6 pgs.

*Journal of Applied Physics*, vol. 77, Jan.1 –15, 1994, "Long pulse electron beam pumped molecular $F_2$ Laser," F.T.J.L. Lankhorst, H.M.J. Bastiaens, H. Botma, P.J.M. Peters, and W.J. Witteman, pp. 399–401.

*Applied Physics Letters*, vol. 51, No. 13, Sep. 28, 1987, "Theoretical evaluation of high–efficiency operation of discharge–pumped vacuum–ultraviolet $F_2$ lasers," Mieko and Minoru Obara, pp. 958–960.

Dupont, et al., "Enhancement of Material Using 248, 308, 532, 1064 nm Laser Pulse with a Water Film on the Surface," *J. Appl. Phys.*, 78 (3), Aug. 1, 1995, pp. 2022–2028.

V.M. Borisov, et al., "Effects Limiting the Average Power of Compact Pulse–Periodic KrF Lasers," *Quantum Electronics*, vol. 25, No. 5, May 1995, pp. 421–425.

*Journal of Applied Physics*, vol. 81, No. 6, Mar. 1997, "Small–signal gain measurements in a discharge–pumped $F_2$ laser," Tahei Kitamura, Yoshihiko Arita and Keisuke Maeda, Masayuki Takasaki, Kenshi Nakamura, Yoshiano Fujiwara and Shiro Horiguchi, 12 pgs.

J.A.R. Samson, "Techniques of Vacuum Ultraviolet Spectroscopy," John Wiley & Sons, New York.

H. Schomalenstroth et al., "Untersuchungen zum Laserstrahlschweissen mit 1–wk–nd:YAG–Laser unter Einsatz verschiedener Schutzgasgemische," *Schweissen & Schneiden*, 49 (1997) Heft 7, pp. 420–424.

"Processing of PTFE with High Power VUV Laser Radiation," D. Basting, U. Sowada, F. Vo__, P. Oesterlin, 3 pgs.

S. Zhu, et al., "Laser Ablation of Solid Substrates in a Water–Confined Environments," *Applied Physics Letters*, vol. 79, No. 9, Aug. 27, 2001, pp. 1396–1398.

\* cited by examiner

157 NM LASER SYSTEM AND METHOD FOR MULTI-LAYER SEMICONDUCTOR FAILURE ANALYSIS

PRIORITY

This application claims the benefit of priority to U.S. provisional patent application no. 60/172,674, filed Dec. 20, 1999, entitled: 157 NM LASER TOOL FOR IC FAILURE ANALYSIS.

FIELD OF THE INVENTION

The present invention relates to failure analysis of integrated circuits (IC's) or other multi-layer solid state devices, and more particularly to the removal of protective (passivation) layers to expose and diagnose underlying circuitry.

BACKGROUND OF INVENTION

During the development process of new multi-layer semiconductor devices, such as integrated circuit devices (IC's), many times the completed IC fails to operate properly. In such a case, the protective (passivation) layer that covers the underlying circuit(s) must be removed. Once exposed, the circuits are analyzed to determine which portion of the circuit was not properly formed (e.g. unwanted electrical short or open circuit). It is important to carefully remove the passivation layer in such a manner that the underlying circuits are not damaged.

Argon Ion, Xenon, Yag and Excimer lasers have been used in IC failure analysis to remove passivation layers. These lasers produce infrared, visible and ultraviolet light that is absorbed by the material used to form the passivation layer. This material is etched (evaporated) away by the laser output with sufficient precision in both location and depth as to expose the underlying circuits without damaging them.

One problem with using a laser system to etch IC materials is that each laser wavelength is ideal for different materials used to form the IC. Therefore, multiple laser wavelengths and systems may be needed depending upon the particular types of materials that are to be etched away.

Recently, $SiO_2$ has become a preferred material used to form the passivation layer. Unfortunately, $SiO_2$ is transparent to the infrared, visible and ultraviolet light produced by Ion, Yag and Excimer layers. Instead of etching the $SiO_2$ material, the laser energy from these systems is transmitted through the passivation layer and causes direct damage to the underlying circuitry. Therefore, those performing failure analysis on IC's using $SiO_2$ have used focused ion beams to etch away the $SiO_2$, where a beam of ions is generated and focused onto the passivation layer.

There are several drawbacks in using focused ion beams in IC failure analysis. First, systems that produce focused ion beams are expensive and cumbersome to use. Second, it takes a relatively long time for the focused ion beam to etch the proper amount of material from the $SiO_2$ layer. Third, and most importantly, the ion beam etch process cannot be optically monitored in the same manner as the laser etching process. With laser etching, the laser beam location and etch process can be optically monitored with an off or on axis camera to ensure the proper amount of material is removed. With ion beam etching, the circuits must be mapped in advanced, and the ion beam directed to the protective layer over the circuits based upon such mapping.

There is a need for a system that accurately and precisely etches $SiO_2$ material from IC's without damaging the underlying circuits, while providing optical monitoring of the etch process. There is also a need for such a system to etch practically all types of materials used in modern integrated circuits, without having to swap laser systems or laser wavelengths.

SUMMARY OF THE INVENTION

The present invention solves the above mentioned problems by providing a laser system and method that utilizes the higher energy 157 nm line from a molecular fluorine ($F_2$) laser to etch and machine IC materials, namely $SiO_2$. The higher energy 157 nm wavelength is strongly absorbed by $SiO_2$ and therefore can selectively remove the $SiO_2$ layer without detrimentally affecting the metal conductors below.

The invention also provides visible red 718 nm radiation from the $F_2$ laser which travels through upper $SiO_2$ protective layer(s) to machine materials found in lower layers of the IC without disturbing the protective layer(s).

The present invention is a method of performing failure analysis upon a multi-layer semiconductor device. The method comprises the steps of exciting a gain medium containing molecular fluorine and disposed in a resonant cavity to generate an output beam having a wavelength around 157 nm, and directing the output beam onto a multi-layer semiconductor device to selectively etch away material therefrom.

In another aspect of the present invention, a failure analysis system includes a resonant cavity, a gain medium containing molecular fluorine and disposed in the resonant cavity, a power supply for exciting the gain medium to generate an output beam having a wavelength around 157 nm, and an imaging system that directs the output beam onto a multi-layer semiconductor device to selectively etch away material therefrom.

In yet another aspect of the present invention, the method of performing failure analysis upon a multi-layer semiconductor device includes the steps of exciting a gain medium containing molecular fluorine and disposed in a resonant cavity to generate an output beam having a wavelength around 157 nm, and directing the output beam onto a multi-layer semiconductor device that includes an integrated circuit covered by a passivation layer, wherein a portion of the passivation layer is etched away by the output beam to expose the integrated circuit.

In still one further aspect of the present invention, a method of etching a passivation layer formed on a semiconductor substrate using a beam of radiation having a wavelength of 157 nm generated from a molecular fluorine laser comprises the steps of directing the beam of 157 nm radiation towards the passivation layer, and selectively removing a portion of the passivation layer using the directed beam.

DETAILED DESCRIPTION OF THE PREFERRED EMBODIMENTS

Figure 1:
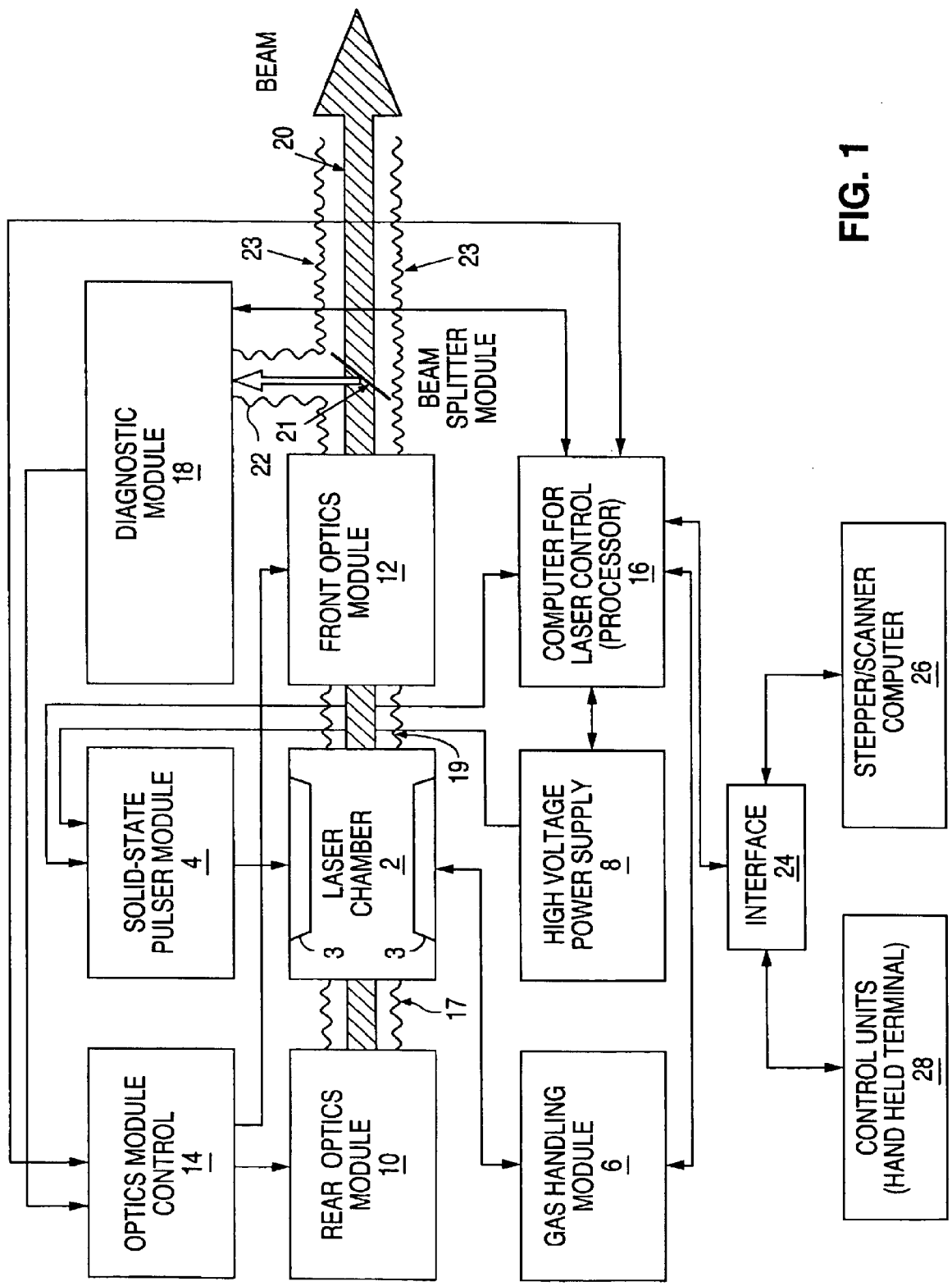
FIG. 1 schematically illustrates a molecular fluorine laser system in accord with a preferred embodiment.

Referring to FIG. 1, a molecular fluorine laser system for deep ultraviolet (DUV) or vacuum ultraviolet (VUV) etching, is schematically shown. The system generally includes a laser chamber 2 having a pair or several pairs of main discharge electrodes 3 connected with a solid-state pulser module 4, and a gas handling module 6. The solid-state pulser module 4 is powered by a high voltage power supply 8. The laser chamber 2 is surrounded by optics module 10 and optics module 12, forming a resonator. The optics modules 10 and 12 are controlled by an optics control module 14.

A computer 16 for laser control receives various inputs and controls various operating parameters of the system. A diagnostic module 18 receives and measures various parameters of the main output beam 20 via a beam splitter module 21 that deflects a small portion 22 of the main beam 20 toward the diagnostic module 18. The main output beam 20 is preferably the laser output to an imaging system and ultimately to a workpiece. The laser control computer 16 communicates through an interface 24 with a stepper/scanner computer 26 and other control units 28.

The laser chamber 2 contains a laser gas mixture and includes a pair (or several pairs) of main discharge electrodes 3 and one or more preionization electrodes (not shown). Preferred main electrodes 3 are described at U.S. patent applications Ser. Nos. 09/453,670, 60/184,705 and 09/453,670, each of which is assigned to the same assignee as the present application and is hereby incorporated by reference. Other electrode configurations are set forth at U.S. Pat. Nos. 5,729,565 and 4,860,300, each of which is assigned to the same assignee, and alternative embodiments are set forth at U.S. Pat. Nos. 4,691,322, 5,535,233 and 5,557,629, all of which are hereby incorporated by reference. The laser chamber 2 also includes a preionization arrangement (not shown). Preferred preionization units are set forth at U.S. patent application Ser. Nos. 09/692,265, 09/532,276, 09/535,276 and 09/247,887, each of which is assigned to the same assignee as the present application, and alternative embodiments are set forth at U.S. Pat. Nos. 5,337,330, 5,818,865 and 5,991,324, all of the above patents and patent applications being hereby incorporated by reference.

The solid-state pulser module 14 and high voltage power supply 8 supply electrical energy in compressed electrical pulses to the preionization and main electrodes 3 within the laser chamber 2 to energize the gas mixture. The preferred pulser module and high voltage power supply is described at U.S. Pat. No. 6,020,723, and alternative embodiments are described at U.S. patent application Ser. Nos. 60/149,392, 60/198,058, 60/204,095, and 09/390,146, and U.S. Pat. No. 6,005,880, each of which is assigned to the same assignee as the present application and which is hereby incorporated by reference into the present application. Other alternative pulser modules are described at U.S. Pat. Nos. 5,982,800, 5,982,795, 5,940,421, 5,914,974, 5,949,806, 5,936,988, 6,028,872 and 5,729,562, each of which is hereby incorporated by reference. A conventional pulser module may generate electrical pulses in excess of 3 Joules of electrical power (see the '988 patent, mentioned above).

The laser chamber 2 is sealed by windows transparent to the wavelength(s) of the emitted laser radiation beam 20. The windows may be Brewster windows or may be aligned at another angle to the optical path of the resonating beam. The beam path between the laser chamber and each of the optics modules 10 and 12 is sealed by enclosures 17 and 19, and the interiors of the enclosures are substantially free of water vapor, oxygen, hydrocarbons, fluorocarbons and the like which otherwise strongly absorb VUV laser radiation.

The output beam 20 impinges upon beam splitter module 21 which includes optics for deflecting a portion 22 of the output beam 20 to the diagnostic module 18, or otherwise allowing the small portion 22 of the outcoupled beam 20 to reach the diagnostic module 18, while a main beam portion 20 is allowed to continue as the output beam of the laser system. Preferred optics include a beamsplitter or otherwise partially reflecting surface optic. The optics may also include a mirror or beam splitter as a second reflecting optic. More than one beam splitter and/or high reflecting mirror(s), and/or dichroic mirror(s) may be used to direct portions of the beam to components of the diagnostic module 18. A holographic beam sampler, transmission grating, partially transmissive reflection diffraction grating, grism, prism or other refractive, dispersive and/or transmissive optic or optics may also be used to separate a small beam portion 22 from the main beam 20 for detection at the diagnostic module 18, while allowing most of the main beam 20 to reach an application process directly or via an imaging system. Alternately, the beam splitter module 21 can reflect the main beam 20 while transmitting a small beam portion 22 to the diagnostic module 18. The portion of the outcoupled beam which continues past the beam splitter module 21 is the output beam 20 of the laser, which propagates toward an industrial or experimental application such as an imaging system and workpiece for photolithographic applications.

Purge/vacuum tubes 23 seal the beam path of the beams 22 and 20 to keep the beam paths free of photoabsorbing species. Smaller enclosures 17 and 19 seal the beam path between the chamber 2 and the optics modules 10 and 12. The preferred purge/vacuum seal enclosure 23 and beam splitting module 21 are described in detail in the Ser. Nos. 09/343,333, 09/594,892 and 09/598,552 applications, incorporated by reference above, and in U.S. patent application Ser. No. 09/131,580, which is assigned to the same assignee and U.S. Pat. Nos. 5,559,584, 5,221,823, 5,763,855, 5,811,753 and 4,616,908, all of which are hereby incorporated by reference. An inert gas purge is preferably flowing through the purge/vacuum seal enclosure 23.

The diagnostic module 18 preferably includes at least one energy detector. This detector measures the total energy of the beam portion 22, which corresponds directly to the energy of the output beam 20. An optical configuration such as an optical attenuator, e.g., a plate or a coating, or other optics may be formed on or near the detector or beam splitter module 21 to control the intensity, spectral distribution and/or other parameters of the radiation impinging upon the detector (see U.S. patent applications Ser. Nos. 09/172,805, 60/172,749, 60/166,952 and 60/178,620, each of which is assigned to the same assignee as the present application and is hereby incorporated by reference).

One other component of the diagnostic module 18 is preferably a wavelength and/or bandwidth detection component such as a monitor etalon or grating spectrometer (see U.S. patent applications Ser. Nos. 09/416,344, 60/186,003, U.S. patent application serial no. not yet assigned, by Kleinschmidt entitled, "Temperature Compensation Method for Wavemeters, filed Oct. 10, 2000, and Ser. Nos. 60/186,096, and 60/202,564, each of which is assigned to the same assignee as the present application, and U.S. Pat. Nos. 4,905,243, 5,978,391, 5,450,207, 4,926,428, 5,748,346, 5,025,445, and 5,978,394, all of the above wavelength and/or bandwidth detection and monitoring components being hereby incorporated by reference).

Other components of the diagnostic module 18 may include a pulse shape detector or ASE detector, such as are described at U.S. patent applications Ser. Nos. 09/484,818 and 09/418,052, respectively, each of which is assigned to the same assignee as the present application and is hereby incorporated by reference, such as for gas control and/or output beam energy stabilization. There may be a beam alignment monitor, e.g., such as is described at U.S. Pat. No. 6,014,206 which is hereby incorporated by reference.

The processor or control computer 16 receives and processes values of some of the pulse shape, energy, amplified spontaneous emission (ASE), energy stability, energy overshoot for burst mode operation, wavelength, spectral purity and/or bandwidth, among other input or output parameters of the laser system and output beam. The processor 16 also controls the power supply 8 and pulser module 4 to control the moving average pulse power or energy, such that the energy dose at points on the workpiece is stabilized around a desired value. In addition, the computer 16 controls the gas handling module 6 which includes gas supply valves connected to various gas sources.

Gas injections, total pressure adjustments and gas replacement procedures are performed using the gas handling module 6, which preferably includes a vacuum pump, a valve network and one or more gas compartments. The gas handling module 6 receives gas via gas lines connected to gas containers, tanks, canisters and/or bottles. Preferred gas handling and/or replenishment procedures of the preferred embodiment, other than as specifically described herein, are described at U.S. Pat. Nos. 4,977,573 and 5,396,514 and U.S. patent applications Ser. Nos. 09/447,882, 09/418,052, 09/379,034, 60/171,717, and 09/588,561, each of which is assigned to the same assignee as the present application, and U.S. Pat. Nos. 5,978,406, 6,014,398 and 6,028,880, all of which are hereby incorporated by reference. A Xe gas supply may be included either internal or external to the laser system according to the '025 application, mentioned above.

The laser gas mixture is initially filled into the laser chamber 2 during new fills. The gas composition for the $F_2$ laser uses either helium, neon, or a mixture of helium and neon as a buffer gas. The concentration of fluorine in the buffer gas preferably ranges from 0.003% to around 1.0%, and is preferably around 0.1%. The addition of a trace amount of xenon, and/or argon, and/or oxygen, and/or krypton and/or other gases may be used for increasing the energy stability, burst control, or output energy of the laser beam. The concentration of xenon, argon, oxygen, or krypton in the mixture may range from 0.0001% to 0.1%. Some alternative gas configurations including trace gas additives are set forth at U.S. patent application Ser. No. 09/513,025 and U.S. Pat. No. 6,157,662, each of which is assigned to the same assignee and is hereby incorporated by reference.

Optics module 12 preferably includes means for outcoupling the beam 20, such as a partially reflective resonator reflector. The beam 20 may be otherwise outcoupled by an intraresonator beam splitter or partially reflecting surface of another optical element, and the optics module 12 would in this case include a highly reflective mirror. The optics control module 14 controls the optics modules 10 and 12 such as by receiving and interpreting signals from the processor 16, and initiating realignment or reconfiguration procedures.

Figure 2:
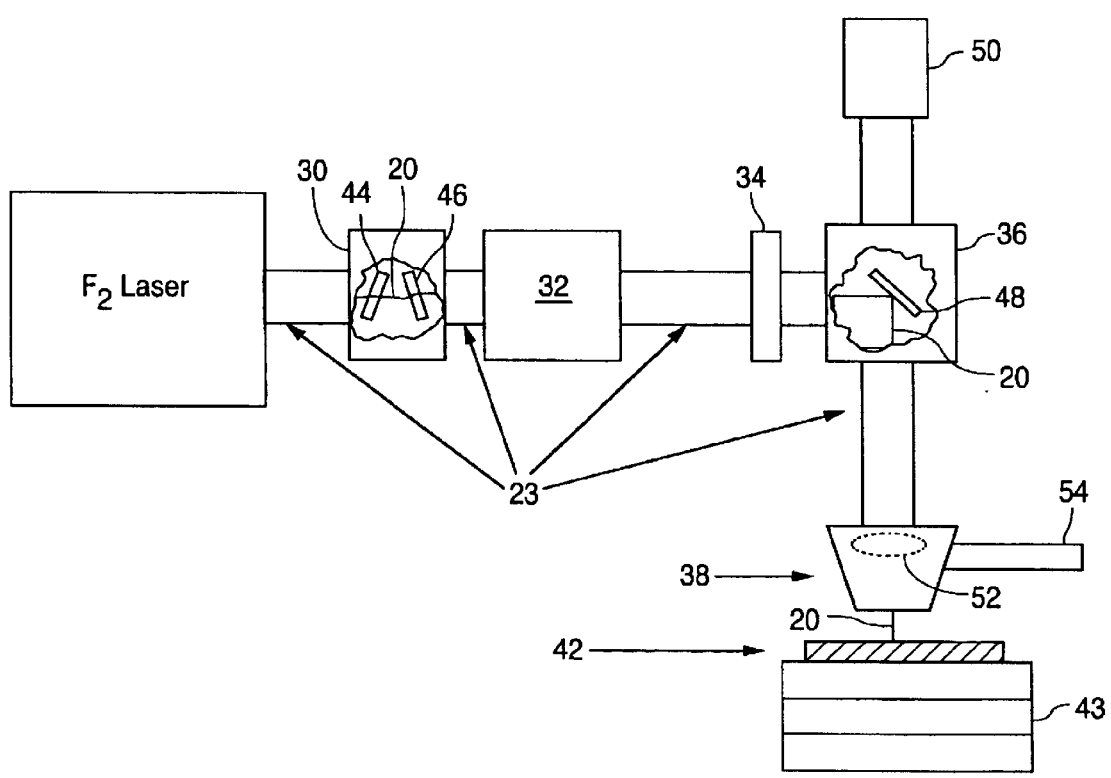
FIG. 2 is a side view of the $F_2$ laser and imaging system of the present invention.

FIG. 2 illustrates the path of output beam 20 once it leaves the $F_2$ laser. Output beam 20 travels through an attenuator 30, homogenizer 32, mask 34, beam turning mirror assembly 36, and out through imaging objective 38 toward the workpiece 42 mounted on an X-Y-Z stage 43. These components are all attached together via purge/vacuum tubes 23 which form a purged beam path for output beam 20.

Beam attenuator 30 is used to control the fluence of the radiation onto the workpiece 42 being evaluated. Some materials require a lower fluence to effectively etch, while other materials need the highest fluence possible. In addition, ablation rates vary as a function of fluence and therefore selective removal can be enhanced for highest quality through beam attenuation. Beam attenuator 30 is preferably a single attenuating optical element 44 with an optical coating whereby the transmission through the optical element 44 varies as a function of the angle of incidence. An uncoated optic 46 matched with the coated optical element 44 is included to compensate for beam walk-off as the coated optical element 44 is tilted to adjust attenuation of beam 20. In addition or alternatively, gas cells can be used to control the attenuation of the beam 20. For example, through careful control of the vacuum or purge of the enclosure tubes 23, trace amounts of a photoabsorbing gas can be injected along the path of beam 20 to absorb a predetermined amount of optical power.

The initial output of the $F_2$ laser typically has a gaussian profile in the short axis and a pseudo top-hat profile in the longer axis. As a consequence, beam homogenizer 32 is introduced to convert output beam 20 to have a top-hat profile in both axes. Homoginizer 32 preferably transmits a beam profile that has a top-hat by top-hat profile to at least better than ±10%, which is considered suitable for uniform ablation for most materials. The homogenizer 32 includes a set of crossed cylindrical lenses, a pair of cylindrical lenses, a pair of bi-prisms, or any other equivalent optical scheme that breaks the initial output beam 20 into multiple beamlets and then recombines them at the plane where the mask is located to have the desired profile.

A beam homoginizer, however, is not always necessary. There are some applications where the majority of the laser's energy can be discarded because the feature being etched is very small, and thus the mask is efficiently illuminated by the center portion of the beam profile (i.e. the size of mask does necessitate more than 10% of the gaussian profile). For example, with an $F_2$ laser with beam dimensions of 3 mm by 7 mm, the 3 mm dimension represents the gaussian beam orientation. If the mask is 100 microns square, then illuminating the mask would result in only 3.3% of the gaussian profile being used. Thus, the central, highest peak energy and most uniform portion of the beam is used, and there would be no need for a homogenizer.

The mask 34 can be any opaque substrate that contains a feature in which the 157 nm radiation can pass through. Typical IC failure analysis utilizes an adjustable slit, which allows square or rectangular features to be made. The masks could, however, be fixed and made out of metal shim stock, dielectric mirror, or metal on a quartz substrate with an etched pattern.

The beam turning assembly 36 directs the main beam 20 down to the imaging objective 38. Preferably, the beam turning assembly 36 includes a beam turning mirror 48 that reflects beam 20 from mask 34 down to imaging objective 38, while also allowing visible light to pass vertically so that a CCD camera 50 can be mounted co-linearly with the final beam trajectory to view the ablation work on the workpiece. Additionally, a reference or pilot laser could be used to illuminate the mask in such a way as to allow the user to shape the mask prior to removing material from the workpiece. The visible light would show up on the CCD camera 50 and be concentric with the 157 nm radiation.

Imaging objective 38 represents the end of the purged/vacuum portion of the system. The imaging objective 38 includes an objective lens 52 that forms a vacuum tight seal with imaging objective 38, which is the final interface to the ambient air in which the workpiece is placed. All components along the beam line (path of output beam 20 from the output of the F$_2$ laser to the objective lens 52, including the enclosure tubes 23) form a beam path enclosure that must provide an inert gas or vacuum environment in order for the 157 nm radiation to propagate from the laser to the workpiece (subject to allowing a little absorptive gas in for attenuation as explained above). A purge nozzle 54 is attached on the end of the imaging objective 38 to flow nitrogen, argon, helium or any inert gas that does not absorb the 157 nm radiation. The gas purge is necessary to constantly displace the ambient oxygen, water vapor and hydrocarbons in the air between the objective lens 52 and the workpiece. The amount of purge necessary is dependent upon the distance between objective 38 and workpiece 42. A few PSI of purge gas is usually enough over a working distance of a few millimeters. Alternately, if the components along the beam path are purged, purge nozzle 54 could be eliminated, and the purge gas from the beam enclosure could flow past the objective lens 52 and toward the workpiece 42.

The F$_2$ laser images the mask onto the workpiece with an energy density sufficient to remove selective layers from the workpiece. The workpiece 42 is any semiconductor device that comprises a plurality of layers of materials, where one or more top layers need to be removed to expose other layers underneath. For the preferred embodiment, the workpiece is an integrated circuit (IC) with a protective passivation layer (e.g. SiO$_2$) covering circuitry formed in layers underneath the passivation layer. Selective material removal from the IC permits the evaluation of a circuitry for shorts and other defects. An in-line or off-axis observation system is included to aid in locating regions of a circuit and the ability to observe the material removal process. The 157 nm output is ideal for this type of work because very few materials are transparent to this vacuum ultraviolet wavelength. Further, the higher energy of this wavelength better and more accurately etches materials used to form semiconductor devices. As a consequence, this radiation can be used for practically all materials used to form semiconductor devices, and especially SiO$_2$ passivation layers. Further, the 157 nm radiation is absorbed within a very shallow depth (10s of nanometers). Thus, the depth of penetration and material removal can be very accurately dictated by the number of pulses incident upon the workpiece. Each pulse has a calculated effect on the etched material. With the preferred embodiment, 0.01 to 0.1 um of SiO$_2$ is etched away with each pulse, where each pulse includes 0.5 to 3 joules/cm$^2$.

The preferred embodiment is further enhanced by utilizing both the molecular fluorine line (157 nm) and the atomic fluorine line (718 nm) of the F$_2$ laser system. A substantial amount of red light around 718 nm is produced by F$_2$ laser systems, whereby the red 718 nm light is usually filtered out from the main output beam. However, with the present invention, the red 718 nm light is useable for alignment purposes, or for passing through the passivation or other layers transparent to red visible light without destroying them, to treat or machine layers underneath these upper layer(s). Either both wavelengths are used simultaneously, or a filter downstream selectively filters out one of the wavelengths. For example, the visible red 718 nm radiation can be transmitted through SiO$_2$ to machine layers beneath the SiO$_2$, without destroying the top SiO$_2$ layer.

While exemplary drawings and specific embodiments of the present invention have been described and illustrated, it is to be understood that that the scope of the present invention is not to be limited to the particular embodiments discussed. Thus, the embodiments shall be regarded as illustrative rather than restrictive, and it should be understood that variations may be made in those embodiments by workers skilled in the arts without departing from the scope of the present invention as set forth in the claims that follow, and equivalents thereof. For example, the F$_2$ used with the present invention could be quite simplified compared to the laser system of FIG. 1. Specifically, a scaled down, air-cooled, system with no energy monitor can be used to produced the 157 nm energy for desired IC material removal.

In addition, in the method claims that follow, the operations have been ordered in selected typographical sequences. However, the sequences have been selected and so ordered for typographical convenience and are not intended to imply any particular order for performing the operations, except for those claims wherein a particular ordering of steps is expressly set forth or understood by one of ordinary skill in the art as being necessary.

What is claimed is:

1. A method of performing failure analysis upon a multi-layer semiconductor device, comprising the steps of:

exciting a gain medium containing molecular fluorine and disposed in a resonant cavity to generate an output beam having a first component with a wavelength around 157 nm, and having a second component with a wavelength around 718 nm;

directing the first component of the output beam onto a multi-layer semiconductor device to selectively etch away a first material therefrom;

directing the second component of the output beam onto the multi-layer semiconductor device to treat a second material of the multi-layer device without etching the first material;

shaping the beam into a pattern using a mask;

imaging the shaped beam onto the semiconductor device; and viewing the etching of the first material using a camera aligned co-linearly with a final trajectory of the output beam.

2. A method of performing failure analysis upon a multi-layer semiconductor device, the method comprising the steps of:

exciting a gain medium containing molecular fluorine and disposed in a resonant cavity to generate an output beam having a first component with a wavelength around 157 nm and having a second component with a wavelength around 718 nm;

directing the output beam onto a multi-layer semiconductor device that includes integrated circuitry covered by a passivation layer, wherein a portion of the passivation layer is etched away by the first component of the output beam to expose the integrated circuitry, and the second component of the output beam is directed onto the multi-layer semiconductor device to provide at least one of the functions, selected from the following group functions: providing a visible light used for alignment of the output beam, and treating layers under the passivation layer without destroying the passivation layer;

shaping the beam into a pattern using a mask;

imaging the shaped beam onto the semiconductor device;

viewing the etching of the material using a camera aligned co-linearly with a final trajectory of the output beam.

3. A method of etching a passivation layer formed on a semiconductor substrate using a beam of radiation having a wavelength of around 157 mm and having a wavelength of around 718 nm, where the beam is generated from a molecular fluorine laser, the method including:

directing the beam of radiation towards the passivation layer;

selectively removing a portion of the passivation layer using the directed beam;

shaping the beam into a pattern using a mask, wherein the directing step includes imaging the shaped beam onto the semiconductor device, and wherein energy of the beam at a wavelength of around 157 nm operates to remove the portion of the passivation layer, and wherein energy of the beam at the wavelength of around 718 nm operates to treat a material disposed under the passivation layer without damaging the passivation layer; and viewing the removal of the passivation layer using a camera aligned co-linearly with a final trajectory of the beam.

* * * * *